US009558405B2

(12) United States Patent
Leong et al.

(10) Patent No.: US 9,558,405 B2
(45) Date of Patent: Jan. 31, 2017

(54) IMAGING BASED INSTRUMENT EVENT TRACKING

(71) Applicant: Analogic Corporation, Peabody, MA (US)

(72) Inventors: David L. Leong, Seabrook, NJ (US); Nicholas A. Accomando, Hingham, MA (US); John P. O'Connor, Andover, MA (US)

(73) Assignee: Analogic Corporation, Peabody, MA (US)

( * ) Notice: Subject to any disclaimer, the term of this patent is extended or adjusted under 35 U.S.C. 154(b) by 79 days.

(21) Appl. No.: 14/598,480

(22) Filed: Jan. 16, 2015

(65) Prior Publication Data

US 2016/0210511 A1    Jul. 21, 2016

(51) Int. Cl.
| | |
|---|---|
| *G06K 9/00* | (2006.01) |
| *G06K 9/46* | (2006.01) |
| *G06K 9/62* | (2006.01) |
| *G06T 7/00* | (2006.01) |

(52) U.S. Cl.
CPC ............ *G06K 9/00624* (2013.01); *G06K 9/46* (2013.01); *G06K 9/4661* (2013.01); *G06K 9/6201* (2013.01); *G06T 7/0014* (2013.01); *G06K 2009/4666* (2013.01)

(58) Field of Classification Search
None
See application file for complete search history.

(56) References Cited

U.S. PATENT DOCUMENTS

| | | | |
|---|---|---|---|
| 6,764,449 B2 | 7/2004 | Lee et al. | |
| 2003/0135119 A1* | 7/2003 | Lee | A61B 8/0833 600/461 |
| 2007/0213139 A1* | 9/2007 | Stivers | A63B 24/0003 473/199 |
| 2008/0232688 A1* | 9/2008 | Senior | G01S 3/7864 382/181 |
| 2010/0054696 A1* | 3/2010 | Doser | G11B 27/10 386/201 |
| 2011/0009748 A1 | 1/2011 | Greene et al. | |

OTHER PUBLICATIONS

Chatelain et al., "Real-time needle detection and tracking using a visually served 3D ultrasound probe", May 2013, Published in Robotics and Automation (ICRA), pp. 1676-1681.*
Wang et al., "Robust guidewire tracking in fluoroscopy", IEEE Computer Society Conference on Computer Vision and Pattern Recognition, Jun. 2009.*

* cited by examiner

*Primary Examiner* — Jason Heidemann
*Assistant Examiner* — Brian Shin
(74) *Attorney, Agent, or Firm* — Anthony M. Del Zoppo, III; Driggs, Hogg, Daugherty & Del Zoppo Co. LPA

(57) ABSTRACT

A method includes obtaining real-time imaging data of at least a sub-portion of an object and a region of interest therein. The method further includes displaying the real-time imaging data as the real-time imaging is obtained. The method further includes tracking extraction of a sample from the region of interest by an extraction device based on the real-time imaging data. The method further includes identifying an extraction location for the extracted sample based on the tracking and the real-time imaging data and generating a signal indicative thereof.

15 Claims, 4 Drawing Sheets

IMAGING BASED INSTRUMENT EVENT TRACKING

TECHNICAL FIELD

The following generally relates to imaging and more particularly to imaging based instrument event tracking, and is described with particular application to ultrasound (US) imaging, although other imaging modalities are contemplated herein.

BACKGROUND

An ultrasound (US) imaging system includes a transducer array that transmits an ultrasound beam into an examination field of view. As the beam traverses structure (e.g., of a sub-portion of an object or subject) in the field of view, sub-portions of the beam are attenuated, scattered, and/or reflected off the structure, with some of the reflections (echoes) traversing back towards the transducer array. The transducer array receives echoes, which are processed to generate an US image of the sub-portion of the object or subject.

US imaging has been used in a wide range of medical and non-medical applications. An example is US guided biopsy. Generally, a biopsy is a procedure in which a small sample (s) of tissue of interest (e.g., prostate, lung, breast, etc.) is removed for subsequent examination for abnormalities such as cancer cells. In one instance, the biopsy instrument includes a trigger configured to actuate a spring-loaded biopsy needle. The needle is inserted through the skin and moved to the target tissue. For the biopsy, the trigger is actuated, which causes a portion of needle that extracts the tissue sample to move into and out of the tissue at a relatively high speed, extracting a sample.

The movement of the needle during tissue extraction can be seen as a white flash under real-time imaging. To record the location of the sample, in one instance the clinician manually marks start and end locations of the biopsy sample on an image based on the trajectory of the needle from visual observation of the event during real-time imaging by the clinician. In another instance, the event occurrence is identified from the sound of the actuated trigger. Unfortunately, these approaches are susceptible to human error and inaccuracy. Thus, they are not well-suited for monitoring the same sample site over time and/or subsequently taking another sample at the same location.

SUMMARY

Aspects of the application address the above matters, and others.

In one aspect, a method includes obtaining real-time imaging data of at least a sub-portion of an object and a region of interest therein. The method further includes displaying the real-time imaging data as the real-time imaging is obtained. The method further includes tracking extraction of a sample from the region of interest by an extraction device based on the real-time imaging data. The method further includes identifying an extraction location for the extracted sample based on the tracking and the real-time imaging data and generating a signal indicative thereof.

In another aspect, a system includes a navigation processor and an instrument tracking processor. The navigation processor displays imaging data of a region of interest, as the image data is acquired. The instrument tracking processor tracks a path of a sample extraction sub-portion into and out of the region of interest during a sample extraction procedure based in the imaging data. The instrument tracking processor generates a signal indicative of a location of the extracted sample in the region of interest based on the tracked path in the imaging data.

In another aspect, a non-transitory computer readable storage medium is encoded with computer executable instructions, which, when executed by a processor, causes the processor to: automatically identify and record a location of a biopsy sample based on real-time imaging data by detecting an occurrence of an intensity value change in the real-time imaging data and computing a characteristics of the intensity value change, wherein the intensity value change is indicative of a biopsy extraction device moving in and out to extract the biopsy sample.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
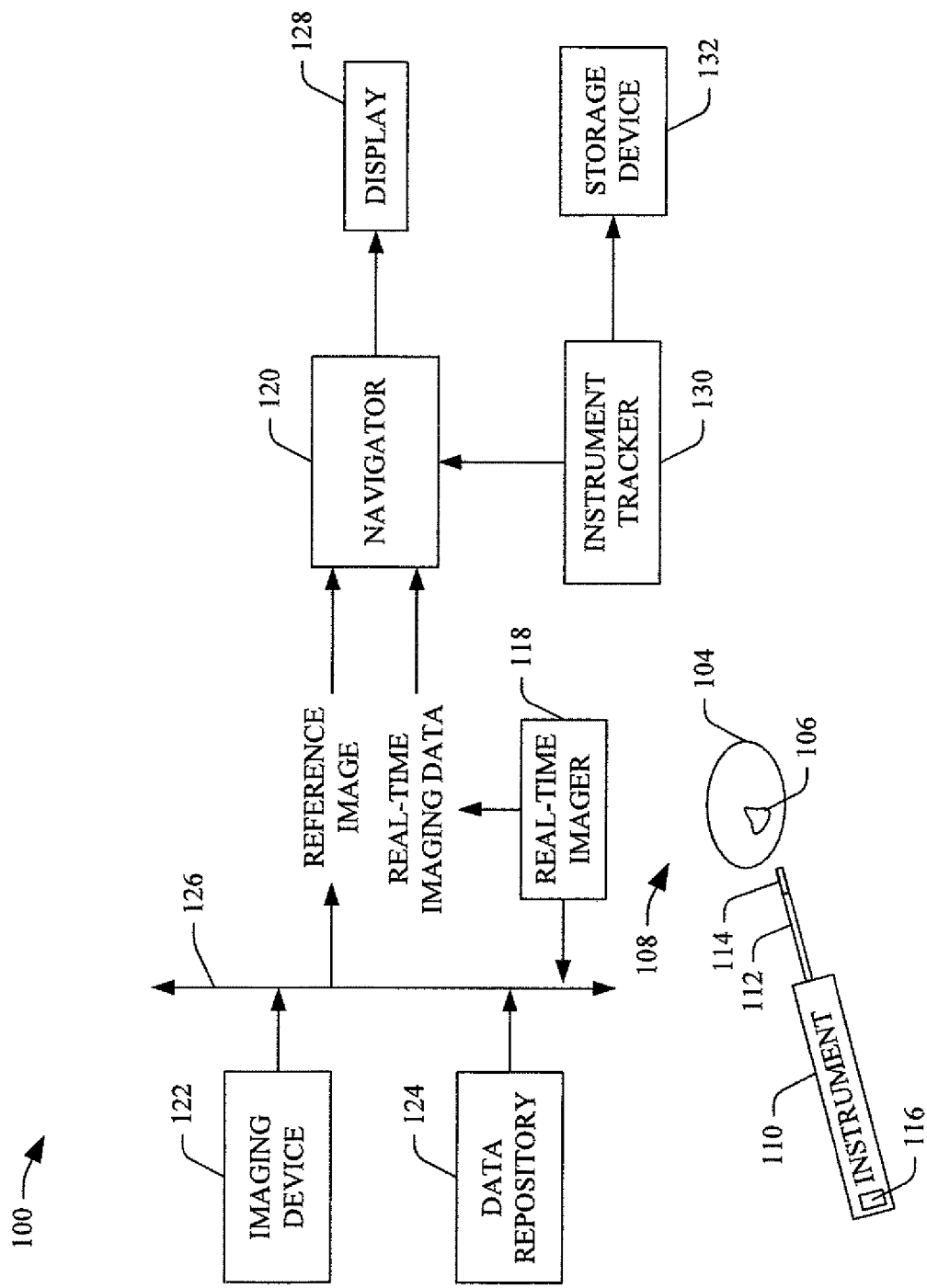
FIG. 1 schematically illustrates an example tracking system for imaging based instrument event tracking.

FIG. 1 schematically illustrates a tracking system 100. The tracking system 100 is configured to track a moving object in a cavity based on real-time imaging. For explanatory purposes and sake of brevity, this will be described below in detail in connection with tracking a sample extraction device and extraction of a sample therewith during a biopsy procedure, including identifying and/or recording the sample extraction location.

An object 104 with a region of interest 106 is in an imaging examination region 108. An instrument 110 includes a biopsy device 112 with a sample extraction sub-portion 114. The instrument further includes an actuator 116 configured to actuate the biopsy device 112 to acquire a sample. For example, where the sample extraction sub-portion 114 includes a spring-loaded needle, the actuator 116 actuates the needle to advance and retract to extract a sample. Other approaches are contemplated herein.

A real-time imager 118 is configured to continuously image (acquire and generate images) of structure in the examination region 108 such as the region of interest 106. However, the real-time imager 118 can alternatively image periodically, on demand, based on a gating signal, etc. The real-time imager 118 can include one or more of an ultrasound (US) imager, a computed tomography (CT) imager, a magnetic resonance (MR) imager, etc. The real-time imager 118 produces real-time image data. As used herein, this means the image is generated and displayed as the raw data is acquired.

A navigator 120 is configured to produce images for guiding the procedure. The navigator 120 receives at least the real-time image data and, optionally, a reference image.

The navigator 120 identifies the region of interest 106 in the real-time image data and/or the reference image. This can be achieved through a manual (i.e., via user interaction) and/or an automatic technique. With automatic techniques, the user can override, modify, discard, etc. an automatically identified region of interest.

Where the navigator receives the real-time image data, the navigator displays the real-time image data as the data is acquired and received. Where the navigator receives the real-time image data and the reference image, the navigator 120 can overlay or superimpose the real-time imaging data of the region of interest 106 over the region of interest 106 in the reference image. For this, the reference image and the real-time imaging data can be registered over successive image frames.

In one instance, the navigator 120 automatically identifies a cloud of keys (e.g., landmarks) distributed within the reference image. The navigator 120 then registers the reference imaging data with the real-time imaging data. An example of such an approach is described in international patent application serial number PCT/US13/72154, entitled "Multi-Imaging Modality Navigation System," and filed on Nov. 27, 2013, which is incorporated herein in its entirety by reference. Other approaches are contemplated herein. The combined data is displayed via a display 128.

The reference image, in one instance, is acquired prior to the procedure, for example, during a planning stage, from a previously performed examination, etc. The reference image can be a 2D, 3D, 4D and/or other image. The reference image can be generated by an imaging device 122 such as US imager, a CT imager, an MR imager and/or other imager such as the real-time imager 118. The reference image can be obtained from the imaging device 122, the real-time imager 118, and/or a data repository 124 (e.g., picture and archiving communication system (PACS), an electronic medical record (EMR), a radiology information system (RIS), etc.), e.g., over a network 126.

An instrument tracker 130 tracks the sample extraction sub-portion 114 during extraction for each sample location. In this example, when the sample extraction sub-portion 114 is at the region of interest 106, the instrument tracker 130 employs a targeting algorithm that determines where and when to take the biopsy sample. In one instance, this determination is followed by either automatic actuation of the actuator 116 through a control signal or alerting the operator to manually actuate the actuator 116.

In another instance, the operator can trigger the actuator 116 based on their assessment that a tip of the sample extraction sub-portion 114 is at a sample extraction location of interest. In another instance, the operator can anticipate the direction and amount of both bending of the sample extraction sub-portion 114 and tissue warping to estimate when the tip is at the sample extraction location of interest and trigger the actuator 116 based thereon. In any case, the movement of the sample extraction sub-portion 114 appears as a white flash in the displayed combined imaging data.

Generally, the white flash represents a change in pixel intensity values due to the presence of the sample extraction sub-portion 114. As described in greater detail below, the instrument tracker 130 tracks the white flash and records the results, which identifies and records the location at which the sample is extracted. It is to be appreciated that knowing the extraction location allows for detailing treatment, for example, where the sample is indicative of tumor cells. For example, such information can be used to drive focal therapy, determine and/or adjust a dose and/or a template for brachytherapy, localize a cryo, RF, microwave, thermal, radiation and/or other ablation, etc.

The results can be conveyed to a storage device 132. For example, the results can be stored either on the fly, as they are acquired, or placed in an information table, either local or remote, for storage at the end of the biopsy. The data can be uploaded in real-time via Ethernet, USB, WI-FI and/or other mediums. For example, in one instance, the results are placed in a local information table, then uploaded via Ethernet at the end of the procedure and stored as metadata in a PACS, an EMR, a RIS, etc., along with other procedure data.

The navigator 120 and/or instrument tracker 130 can be implemented via one or more computer processors (e.g., a central processing unit (CPU), a microprocessor, a controller, etc.) executing one or more computer executable instructions embedded or encoded on non-transitory computer readable storage medium, which excludes transitory medium, but includes physical memory. However, at least one of the computer executable instructions can alternatively be carried by a carrier wave, signal, and/or other transitory medium.

Figure 2:
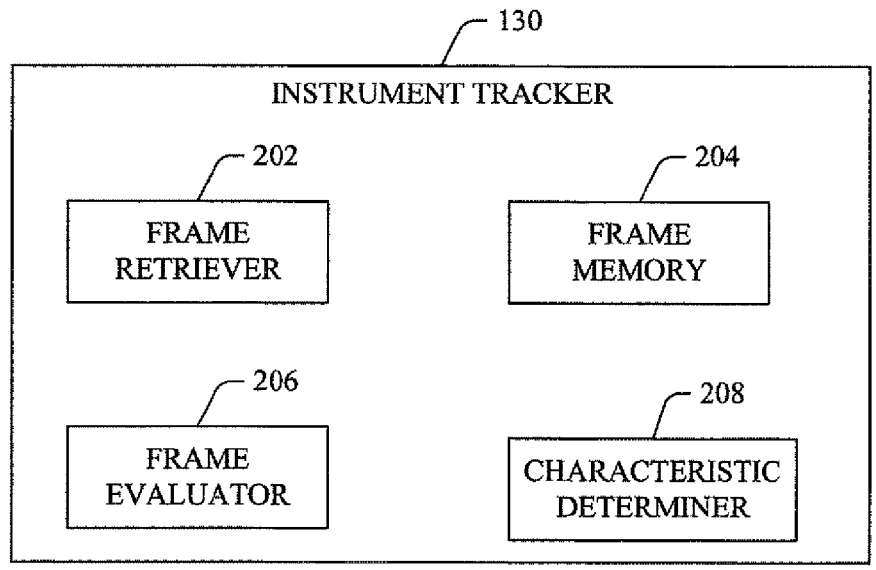
FIG. 2 schematically illustrates an example instrument tracker.

FIG. 2 schematically illustrates a non-limiting example of the instrument tracker 130. The illustrated example includes a frame retriever 202, which retrieves successive frames of the real-time imaging data. The instrument tracker 130 further includes frame memory 204 that stores the retrieved frames. The instrument tracker 130 further includes frame evaluator 206 that evaluates the frames and detects the white flash corresponding to the actuate sample extraction sub-portion 114.

This may include comparing intensities values in successive frames and identifying frames in which an intensity value difference exceeds a pre-determined threshold indicative of a presence of the sample extraction sub-portion 114. The instrument tracker 130 further includes a characteristic determiner 208 that determines one or more characteristics of the white flash, such as the flash boundary and/or centroid, and automatically determines the extraction location and/or a time of the extraction based thereon.

As a tip of the sample extraction sub-portion 114 moves in and out of the region of interest 106 the tip location is tracked through successive frames. Knowing a maximum travel distance of the sample extraction sub-portion 114 relative to the biopsy device 112 allows calculation of a location and a time of the actual sample extraction. This can be achieved, e.g., by extrapolation between a frame in which a distance decrease begins and a prior frame, in which a distance is still increasing. Other approaches are also contemplated herein. The range of the tracking can be limited based on an expected trajectory of the sample extraction sub-portion 114, which can be based on an image based tracking technology, a needle guide, etc.

The location of the extracted sample can be identified (e.g., with alpha-numeric, graphical, and/or other indicia) on the reference image, one or more frames of the real-time imaging data, the combined image, etc. and/or otherwise conveyed, as described herein. Furthermore, text describing the location of the extraction can be incorporated into an electronically formatted report, for example, created during and/or after the biopsy procedure, etc.

Figure 3:
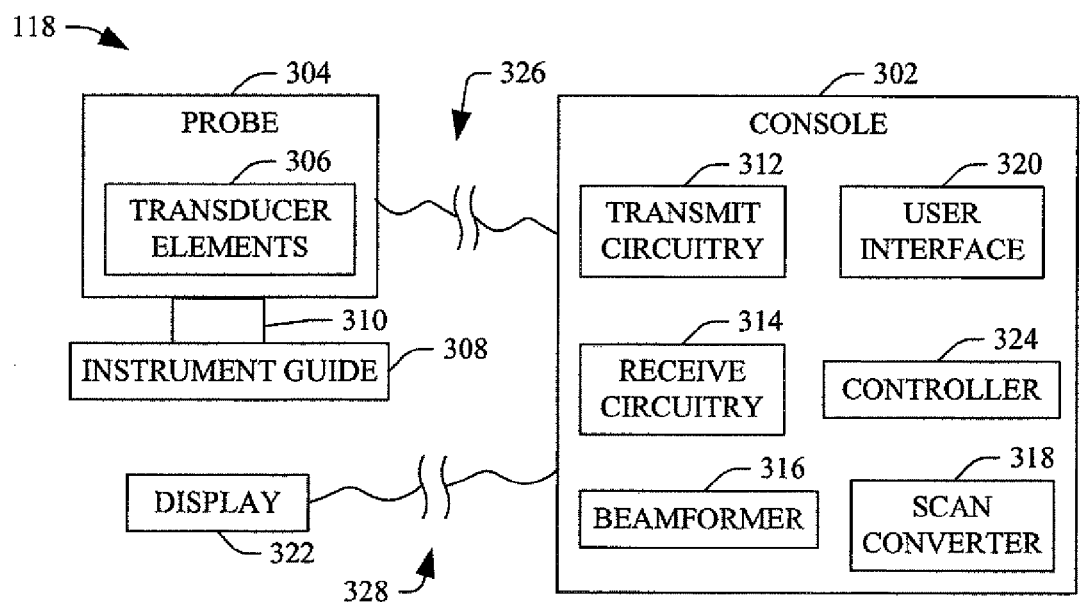
FIGS. 3, 4 and 5 schematically illustrate example US imaging systems.

FIG. 3 illustrates an example where the real-time imager 118 is an US imaging system, which includes a console 302 and a separate US transducer probe 304 that interfaces therewith.

The ultrasound transducer probe 304 includes a transducer array with a plurality of transducer elements 306. The transducer array can be linear, curved, and/or otherwise shaped, fully populated, sparse and/or a combination thereof, etc. The transducer elements 306 can be operated in 2D and/or 3D mode. The transducer elements 306 transmit ultrasound signals and receive echo signals.

An instrument guide 308, such as a biopsy needle guide, is affixed to the US transducer probe 304 through a coupling 310 such as a bracket, clamp, etc. In one instance, the biopsy needle is supported in the instrument guide 308 in a retracted position until a target tissue of interest is located with the US transducer probe 304 as described herein. Then, the needle is advanced to acquire the sample of the target tissue of interest.

Transmit circuitry 312 selectively actuates or excites one or more of the transducer elements 306. More particularly, the transmit circuitry 312 generates a set of pulses (or a pulsed signal) that are conveyed to the transducer elements 306. The set of pulses actuates a set of the transducer elements 306, causing the transducer elements 306 to transmit ultrasound signals into an examination or scan field of view.

Receive circuitry 314 receives a set of echoes (or echo signals) generated in response to the transmitted ultrasound signals. The echoes, generally, are a result of the interaction between the emitted ultrasound signals and the object (e.g., flowing blood cells, organ cells, etc.) in the scan field of view. The receive circuit 314 may be configured for spatial compounding, filtering (e.g., FIR and/or IIR), and/or other echo processing.

A beamformer 316 processes the received echoes. In B-mode, this includes applying time delays and weights to the echoes and summing the delayed and weighted echoes. A scan converter 318 scan converts the data for display, e.g., by converting the beamformed data to the coordinate system of a display or display region used to visually present the resulting data.

A user interface (UI) 320 include one or more input devices (e.g., a button, a knob, a slider, etc., touchscreen and/or physical mechanical device) and/or one or more output devices (e.g., a liquid crystal display, a light emitting diode, etc.), which allows for interaction with the system 118. A display 322 visually displays the US imaging data.

A controller 324 controls the various components of the system 118. For example, such control may include actuating or exciting individual or groups of transducer elements of the probe 304 for an A-mode, B-mode, C-plane, and/or other data acquisition mode, steering and/or focusing the transmitted signal, etc., actuating the transducer elements 306 for steering and/or focusing the received echoes, etc.

The US probe 304 and the display 322 are physically separate electromechanical components with respect to the console 302. The US probe 304 and the display 322 communicate with the console 302 through communications paths 326 and 328. The communications paths 326 and 328 can be wired (e.g., a physical cable and connectors) and/or wireless.

Figure 4:
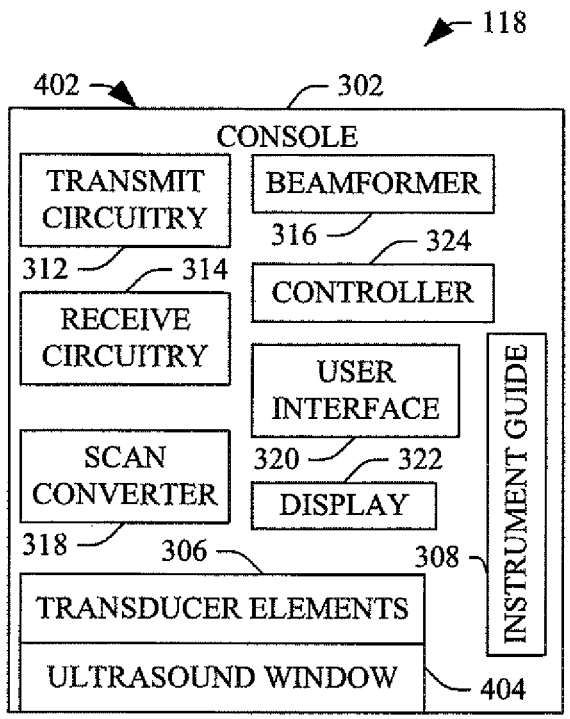

FIG. 4 illustrates a variation of the real-time imager 118. In this example, the console 302 includes a single housing 402. The single housing 402 houses and physically supports the transducer elements 306, the instrument guide 308, the transmit circuitry 312, the receive circuitry 314, the beamformer 316, the scan converter 318 and the controller 324, all of which are inside the single housing 402.

The user interface 320 and/or the display 322 are part of the housing 402. For example, the display 322, in one instance, is a sub-portion of one of the sides of the housing 402. The user interface 320 may include physical mechanical controls at other locations of the housing 402. An ultrasound window 404 is also part of or integrated with the console 302. In this instance, the transducer elements 306 are disposed in the housing 402 behind the ultrasound window 404 and emit signals and receive echoes there through.

In FIG. 4, the real-time imager 118 is a hand-held ultrasound apparatus, which uses internally located power, e.g., from a power source such as a battery, a capacitor, etc. to power the components therein, and/or power from an external power source. An example of a hand-held device are described in U.S. Pat. No. 7,699,776 to Walker et al., entitled "Intuitive Ultrasonic Imaging System and Related Method Thereof," and filed on Mar. 6, 2003, which is incorporated herein in its entirety by reference.

An example of hand-held ultrasound apparatus with an internal instrument guide is described in Ser. No. 13/017,344 to O'Connor, entitled "Ultrasound imaging apparatus," and filed on Jan. 31, 2011, and an example with an external instrument guide is described in U.S. Pat. No. 8,226,562 to Pelissier, entitled "Hand-Held Ultrasound System Having Sterile Enclosure," and filed on Aug. 7, 2008, both of which are incorporated herein in their entirety by reference.

Figure 5:
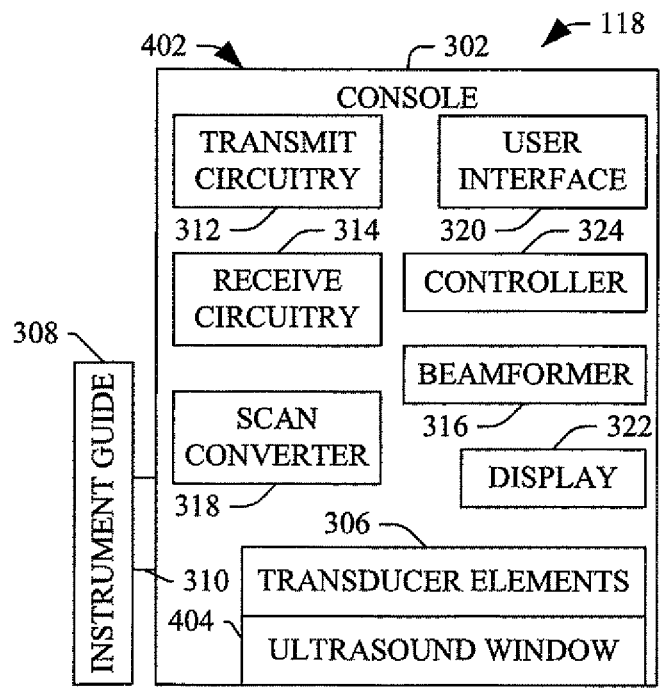

FIG. 5 illustrates a variation of FIG. 4 in which the instrument guide 308 is disposed out of the single housing 402 and affixed thereto through the coupling 310.

Although the approach described herein does not require the use of an external tracking system and/or electro-mechanical sensors, an external tracking system and/or electro-mechanical sensors can be used with the approach described herein. For example, where the instrument guide is not part of the real-time imager 118 or affixed thereto, electro-mechanical sensors affixed to the instrument can be registered to the 3D non-US imaging data coordinate system and used to the track the instrument.

Figure 6:
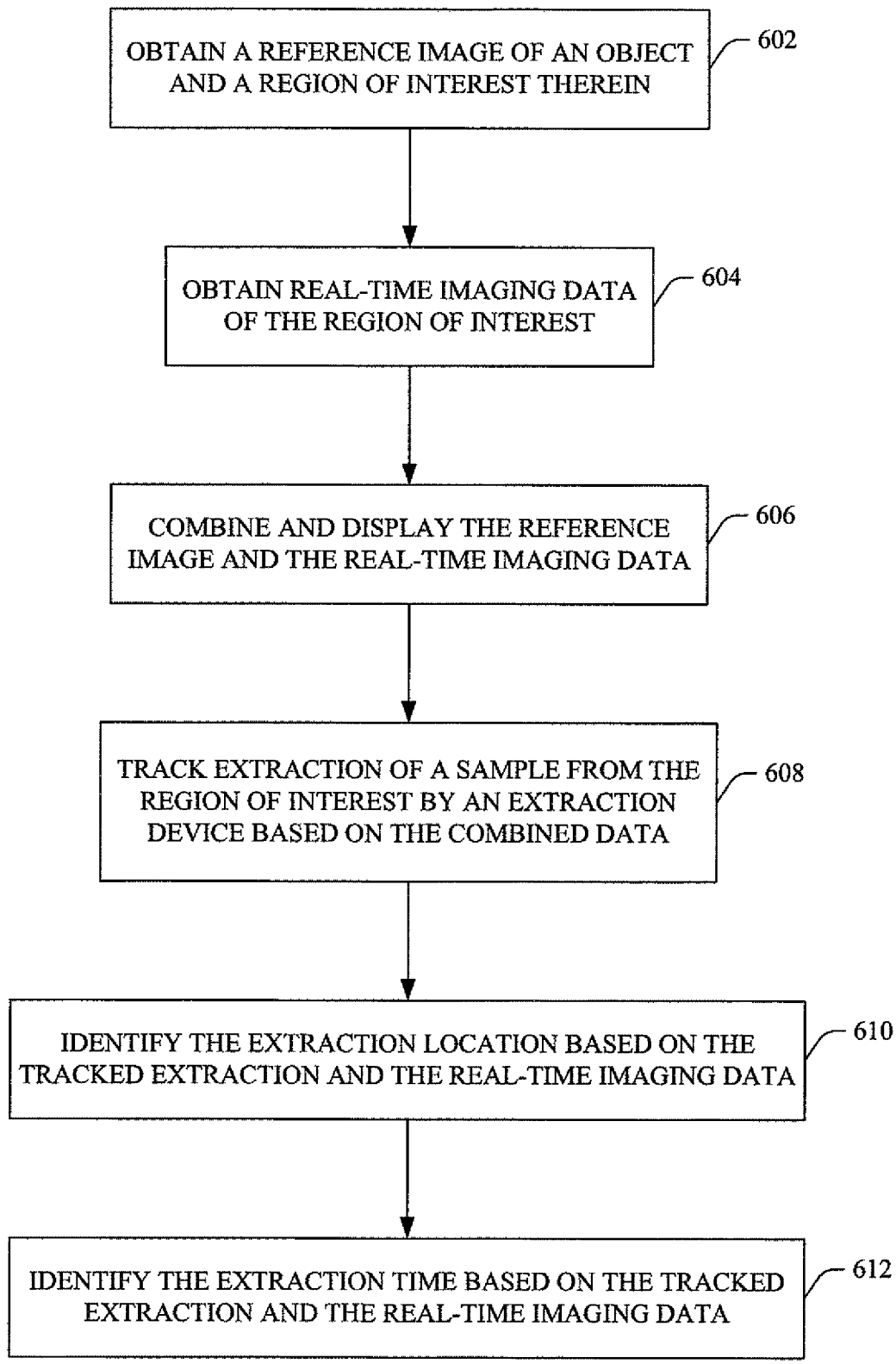
FIG. 6 illustrates an example method for imaging based instrument event tracking.

FIG. 6 illustrates an example method for imaging based instrument tracking.

It is to be appreciated that the ordering of the following acts is for explanatory purposes and is not limiting. As such, one or more of the acts can be performed in a different order, including, but not limited to, concurrently. Furthermore, one or more of the acts may be omitted and/or one or more other acts may be added.

At 602, a reference image of an object and a region of interest therein are obtained.

At 604, real-time imaging data of the object and the region of interest are obtained.

At 606, the reference image and the real-time imaging data of the region of interest are combined and displayed.

At 608, extraction of a sample from the region of interest by an extraction device is tracked based on the combined data, as described herein.

At 610, the extraction location is identified based on the tracking and the real-time imaging data.

At 612, the extraction time is identified based on the tracking and the real-time imaging data.

The extracted location is stored, processed, and/or otherwise utilized, for example, to tailor treatment of a tumor.

In a variation, act 602 is omitted, and the tracking is based on the real-time imaging and not the combined data or reference image.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A method, comprising:
   acquiring, with a transducer array, frames of real-time imaging data of at least a sub-portion of an object and a region of interest therein during a procedure;
   displaying the real-time imaging data as the real-time imaging data is obtained;
   tracking extraction of a sample from the region of interest by an extraction device based on the real-time imaging data by:
      comparing intensity values of pairs of successive frames of the acquired frames;
      indentifying a pair of frames of the acquired frames in which an intensity value difference in the region of interest between the pair of successive frames exceeds a pre-determined threshold, which indicates a transition from an absence of an extraction sub-portion of the extraction device in the region of interest to a presence of the extraction sub-portion in the region of interest;
      indentifying a first frame, which is acquired after the indentified pair of frames, in which a length of the extraction sub-portion increases in the region of interest from a first direction relative to the extraction device, from a comparison of intensity values of the first frame and a frame preceding the first frame;
      indentifying a second frame, which is acquired after the indentified first frame, in which the length of the extraction sub-portion decreases in the region of interest from the first direction relative to the extraction device, from a comparison of intensity values of the second frame with a frame preceding the second frame;
      determining a maximum travel distance of the extraction sub-portion by extrapolation between the first and second identified frames;
      computing a location of the extracted sample in the region of interest with the maximum travel distance; and
      computing a time of the extraction based on a first time of the first frame and a second time of the second frame; and
   storing the location of the extracted sample and the time of the extraction with the acquired frames.

2. The method of claim 1, further comprising:
   determining an extraction boundary based on the first and second frames.

3. The method of claim 1, further comprising:
   determining an extraction centroid based on the first and second frames.

4. The method of claim 1, further combining comprises:
   obtaining a reference image of the object with the region of interest therein;
   combining the reference image and the real-time imaging data, constructing combined data;
   displaying the combined data;
   tracking extraction of the sample from the region of interest by the extraction device based on the combined data; and
   identifying the extraction location for the extracted sample based on the tracking and the real-time imaging data and generating the signal indicative thereof.

5. The method of claim 4, wherein the combining comprises:
   identifying the region of interest in the reference image;
   registering the real-time imaging data with the region of interest in the reference image over successive frames; and
   overlaying the real-time imaging data over the reference image based on the registration.

6. The method of claim 5, wherein the registering comprises:
   identifying a cloud of landmarks distributed within the reference image; and
   registering the reference imaging data with the real-time imaging data based on the identified cloud of landmarks.

7. The method of claim 4, further comprising:
   acquiring the reference image with at least one of an ultrasound scanner, a computed tomography scanner, or a magnetic resonance scanner.

8. The method of claim 1, further comprising:
   acquiring the real-time imaging data with an ultrasound scanner.

9. A system, compridsing:
   a navigation processor that displays frames of real-time imaging data of at least a sub-portion of an object and of a region of interest, as the image data is acquired during a procedure; and
   an instrument tracking processor that:
      compares intensity values of pairs of successive frames of the acquired frames;
      identifies a pair of frames of the acquired frames in which an intensity value difference in the region of interest between the pair of successive frames exceeds a pre-determined threshold, which indicates a transition from an absence of a sample extraction sub-portion of an extraction device in the region of interest to a presence of the sample extraction sub-portion in the region of interest;
      identifies a first frame, which is acquired after the identified pair of frames, in which a length of the extraction sub-portion increases in the region of interest from a first direction relative to the extraction device, from a comparison of intensity values of the first frame and a frame preceding the first frame;
      identifies a second frame, which is acquired after the identified first frame, in which the length of the extraction sub-portion decreases in the region of interest from the first direction relative to the extraction device, from a comparison of intensity values of the second frame with a frame preceding the second frame;
      determines a maximum travel distance of the extraction sub-portion in the region of interest by extrapolation between the first and second indentified frames;
      computes a location of the extracted sample in the region of interest with the maximum travel distance; and
      computes a time of the extraction based on a first time of the first frame and a second time of the second frame; and stores the location of the extracted sample and the time of the extraction with the acquired frames.

10. The system of claim 9, wherein the instrument tracking processor, during the extraction, identifies a frame of the imaging data in which a tip of the sample extraction sub-portion advances in the region of interest and a subsequent frame of the imaging data in which the tip of the sample extraction sub-portion retracts in the region of interest.

11. The system of claim 10, wherein the instrument tracking processor computes the location of the extracted sample in the region of interest based on the frame and the subsequent frame.

12. The system of claim 10, wherein the instrument tracking processor computes the time of the extraction based on the frame and the subsequent frame.

13. The system of claim 10, wherein the instrument tracking processor computes an extraction boundary in the region of interest based on the frame and the subsequent frame.

14. The system of claim 10, wherein the instrument tracking processor computes an extraction centroid in the region of interest based on the frame and the subsequent frame.

15. A non-transitory computer readable storage medium encoded with computer executable instructions, which, when executed by a processor, causes the processor to:
  acquire frames of real-time imaging data of at least a sub-portion of an object and a region of interest therein during a procedure;
  track extraction of a sample from the region of interest by an extraction device based on the real-time imaging data by:
    comparing intensity values of pairs of successive frames of the acquired frames;
    indentifying a pair of frames of the acquired frames in which an intensity value difference in the region of interest between the pair of successive frames exceeds a pre-determined threshold, which indicates a transition from an absence of an extraction sub-portion of the extraction device in the region of interest to a presence of the extraction sub-portion in the region of interest;
    indentifying a first frame, which is acquired after the identified pair of frames, in which a length of the extraction sub-portion increases in the region of interest from a first direction relative to the extraction device, from a comparison of intensity values of the first frame and a frame preceding the first frame;
    indentifying a second frame, which is acquired after the identified first frame, in which the length of the extraction sub-portion decreases in the region of interest from the first direction relative to the extraction device, from a comparison of intensity values of the second frame with a frame preceding the second frame;
    determining a maximum travel distance of the extraction sub-portion by extrapolation between the first and second indentified frames;
    computing a location of the extracted sample in the region of interest with the maximum travel distance; and
    computing a time of the extraction based on a first time of the first frame and a second time of the second frame; and
  store the location of the extracted sample and the time of the extraction with the acquired frames.

* * * * *